United States Patent [19]

Ferraro et al.

[11] 3,957,067

[45] May 18, 1976

[54] DURABLE DENTAL FLOSS

[76] Inventors: Kenneth N. Ferraro; Betty Nell Ferraro, both of 7900 E. 4th Place, Downey, Calif. 90241

[22] Filed: Apr. 16, 1975

[21] Appl. No.: 568,407

[52] U.S. Cl. ................................................ 132/89
[51] Int. Cl.² ........................................ A61C 15/00
[58] Field of Search ........................... 132/89, 91, 92

[56] References Cited
UNITED STATES PATENTS

| | | | |
|---|---|---|---|
| 3,771,536 | 11/1973 | Dragan | 132/89 |
| 3,789,858 | 2/1974 | Pesce | 132/89 |
| 3,800,812 | 4/1974 | Jaffe | 132/89 |
| 3,838,702 | 10/1974 | Standish | 132/89 |

*Primary Examiner*—G. E. McNeill
*Attorney, Agent, or Firm*—Lyon & Lyon

[57] ABSTRACT

A durable dental floss comprised of aromatic polyamide fibers having at least 85 percent of the amide linkages attached directly to two aromatic rings. The floss is heat stable, hydrophobic and has a high tenacity.

6 Claims, No Drawings

DURABLE DENTAL FLOSS

BACKGROUND OF THE INVENTION

The present invention relates to dental floss and, in particular, relates to a dental floss comprised of aromatic polyamide fibers having at least 85 percent of the amide linkages attached directly to two aromatic rings.

The use of dental floss is essential to oral health. Dental floss functions to cleanse dental or bacterial plaque from certain critically important areas in dentition and supporting structures surrounding the teeth. Bacterial plaque is comprised of salivary biproducts, dead epithelial cells and bacteria. Bacterial plaque organizes into colonies on the surface of the tooth within 24 to 36 hours irrespective of nutrient intake. Upon contact with carbohydrates, the bacterial colonies form acids which cause destruction of the tooth structure. Bacterial colonies also produce bacterial toxins which, in some cases, cause periodontal disease or pyorrhea. This disease results in inflamed gum tissues which, in some cases, causes recession and destruction of the supporting bone of the tooth or teeth.

These problems can be avoided by daily mechanical disruption of the plaque. Disruption of the plaque functions to disperse the bacterial colonies, thereby preventing the formation of concentrated solutions of acid and bacterial toxins. On most of the dental surface area, bacterial colonies can be disturbed by regular brushing with a tooth brush. Unfortunately, brushing does not disturb bacterial plaque disposed in sheltered or tightly contacting areas of adjacent teeth. Dental floss functions to disturb the colonies of bacteria in these areas.

Dental floss should exhibit certain physical and mechanical properties to enable its use in dental hygiene. Dental floss should possess a high tensile strength or tenacity and should be capable of retaining its tenacity when wet. The dental floss should be heat stable to enable sterilization. Dental floss should not be abrasive enough to cause destruction of the supporting structure of the dentition with continuous use.

One prior dental floss is comprised of silk fibers. Silk has a comparatively low tenacity, which results in frequent breakage during use. Furthermore, the tenacity decreases upon the wetting of the floss thereby enhancing the probability of breakage. Since flossing of the dentition is at best a tedious chore, frequent breakage of the floss during use causes frustration to the user which will, in many cases, result in eventual discontinuation of the use of dental floss. This motivational problem has, in the past, prevented widespread use of dental floss.

Another prior dental floss is comprised of nylon. Nylon also has a comparatively low tenacity which again results in frequent breakage of the floss during use. The tenacity of nylon also decreases upon wetting with saliva thereby enhancing the probability of breakage. In order to prevent the snagging and breaking of the nylon fibers in interstices between the teeth, nylon floss has, in the past, been provided with a lubricant such as a resinous agent or paraffin. The lubricant aids in preventing snagging of the fiber in tight contact areas. Unfortunately, the lubricant becomes displaced onto the surface of the tooth causing a subsequent build-up of a sticky film which acts as a substrate for bacterial growth. The lubricant also prevents the flaring or spreading of the fibers of the floss over the surface of the tooth during use. It is preferred that during use the fibers of the floss spread out on the surface of the tooth thereby enabling every fiber to contact the surface of the tooth. The flaring of the floss over the surface of the tooth enables more efficient disruption of the bacterial plaque. Nylon floss is also abrasive enough that in some cases, it causes partial destruction of the supporting root structure of dentition with continuous use. Nylon polymer is not heat stable enough to enable sterilzation of the floss.

SUMMARY OF THE INVENTION

It is therefore an object of the present invention to provide a heat stable, hydrophobic dental floss which has a high tenacity and is not overly abrasive.

These and other objects and advantages are obtained by forming a dental floss from aromatic polyamides where at least 85 percent of the amide linkages are attached directly to two aromatic rings. Fibers comprised of these types of compounds have been designated as aramids by the Federal Trade Commission. Although the dental floss of the present invention may be fabricated from any aramid, it is preferred that the aramid be comprised of the condensation polymer of terephthalic acid and a diamine such as an aromatic diamine.

Aramids possess many properties which makes their use as dental floss desirable. For example, aramids possess a comparatively high tenacity which is not reduced upon wetting. Aramids are also heat stable enough to enable their sterilization and they are not abrasive enough to cause destruction of the supporting root structure with continuous use.

A more thorough disclosure of the objects and advantages of the present invention is presented in the detailed description which follows.

DETAILED DESCRIPTION OF THE INVENTION

The present invention contemplates the formation of a durable, heat stable dental floss comprised of aromatic polyamides where at least 85 pecent of the amide linkages are attached directly to two aromatic rings. Fibers comprised of these types of compounds have been designated as aramids by the Federal Trade Commission. Although the present invention contemplates the use of any aramid, it is preferred that the aramid be comprised of the condensation polymer of terephthalic acid and a diamine such as an aromatic diamine. It is preferred that the aramid have a tenacity of approximately 20 to 24 grams per denier. It is also preferred that the aramid be capable of forming a fiber having a comparatively small diameter, preferably approximately 0.00047 inches. An aramid which has been found to be suitable for the present invention is that manufactured and marketed by Du Pont under the tradename "Kevlar".

Aramids exhibit unique properties which makes their use as a dental floss desirable. Firstly, aramids have a tensile strength or tenacity which is much greater than prior fibers used for dental flosses. The high tensile strenth enables the use of thinner fibers thereby enabling the formation of floss having a greater number of fibers. The greater number of fibers enables more efficient spreading or flaring of the fibers of the floss over the surface of the tooth during use. This results in more efficient disruption of the bacterial colonies. The high tenacity also makes it unnecessary to lubricate the floss to prevent breakage thereby precluding the build-up of a sticky film on the surface of the teeth and enabling the flaring of the fibers during use. Lastly, the higher tenacity prevents continuous breakage of the floss during use thereby solving the motivational problems encountered with previous dental flosses. Aramids are also less abrasive than nylon fibers thereby avoiding destruction of the supporting structure of the dentition with continuous use of the floss. Aramids are also heat stable enabling sterilization of the floss without loss of desirable properties. Aramids are also inert to water thereby preventing the loss of tenacity upon contact with saliva.

To form the floss of the present invention, it is preferred that an aramid fiber be obtained from a commercial source such as Du Pont. The aramid fiber which is preferably 400 denier is then processed into dental floss by first winding the fiber onto a stationary metal spindle. The end of the fiber is then drawn through guides to a motor driven textile twisting machine. The twisting machine operates to rewind the fiber and to impart preferably five uniform twists per inch to the previously untwisted fiber. The twisting functions to provide a cohesive property to the numerous filaments comprising the fiber. The fiber is than placed in an oven at an elevated temperature, preferably approximately 350°F. for a short period of time, preferably approximately two hours. The heating functions to set the twist in the fiber preventing unravelling when the fiber is removed from its supported state. The fiber is then wound onto a bobbin, sterilized, inspected and packaged. It is preferred that the floss be marketed in a polyethylene package having a snap-on lid. The lid is preferably provided with a cutting edge and an aperture through which the fiber may be drawn.

While an embodiment and application of this invention has been shown and described, it will be apparent to those skilled in the art that many more modifications are possible without departing from the inventive concepts herein described. The invention, therefore, is to be limited only by the lawful scope of the claims which follow.

I claim:

1. A dental floss consisting essentially of an aramid.
2. A dental floss as in claim 1 wherein said floss has a tenacity of approximately 20 to 24 grams per denier.
3. A dental floss as in claim 1 wherein said aramid is comprised of the condensation polymer of terephthalic acid and a diamine.
4. The dental floss of claim 3 wherein said diamine is an aromatic diamine.
5. A dental floss consisting essentially of an aramid comprising the condensation polymer of terephthalic acid and an aromatic diamine, said floss having a tenacity of approximately 20 to 24 grams per denier.
6. The dental floss of claim 5 wherein said floss is provided with five heat set twists per inch.

* * * * *